United States Patent
Rouillon et al.

(10) Patent No.: US 9,933,438 B2
(45) Date of Patent: Apr. 3, 2018

(54) METHOD FOR DIAGNOSING MUSCULAR DYSTROPHY

(71) Applicant: GENETHON, Evry (FR)

(72) Inventors: Jérémy Rouillon, Corbeil-Essonnes (FR); Fedor Svinartchouk, Villejuif (FR)

(73) Assignee: GENETHON, Evry (FR)

( * ) Notice: Subject to any disclaimer, the term of this patent is extended or adjusted under 35 U.S.C. 154(b) by 0 days.

(21) Appl. No.: 14/431,030

(22) PCT Filed: Sep. 26, 2013

(86) PCT No.: PCT/FR2013/052280
§ 371 (c)(1),
(2) Date: Mar. 25, 2015

(87) PCT Pub. No.: WO2014/049282
PCT Pub. Date: Apr. 3, 2014

(65) Prior Publication Data
US 2015/0241452 A1    Aug. 27, 2015

(30) Foreign Application Priority Data
Sep. 26, 2012 (FR) .................................. 12 59023

(51) Int. Cl.
| G01N 33/68 | (2006.01) |
| G01N 27/447 | (2006.01) |
| H01J 49/16 | (2006.01) |

(52) U.S. Cl.
CPC ....... *G01N 33/6893* (2013.01); *G01N 27/447* (2013.01); *G01N 33/6887* (2013.01); *H01J 49/164* (2013.01); *G01N 2333/4712* (2013.01); *G01N 2800/10* (2013.01); *G01N 2800/2878* (2013.01); *G01N 2800/52* (2013.01)

(58) Field of Classification Search
CPC ............ C12N 15/113; C12N 2310/315; C12N 2310/321; C12Q 1/6883; A61K 45/06; A61K 2300/00
See application file for complete search history.

(56) References Cited

U.S. PATENT DOCUMENTS 4,444,879 A * 4/1984 Foster .................. G01N 33/545
                                                   422/400
6,103,466 A * 8/2000 Grobet ................. C07K 14/495
                                                   435/6.11

FOREIGN PATENT DOCUMENTS

EP            2 407 784           1/2012

OTHER PUBLICATIONS

Cuccurullo et al. (Journal of Nephrology, 2010, 23 (S16):S199-S212).*
Matsumura et al. (Journal of the Neurological Sciences, 1989, vol. 93, pp. 147-156).*
Vassiliadis et al. (Journal of Translational Medicine, Jul. 2012, vol. 10, pp. 1-10).*
Cuccurullo et al. (Journal of Nephrology 2010; 23 (S16): S199-S212).*
Nadarajah et al. (Neuromuscular Disorders, vol. 21, 2011, pp. 569-578).*
Vassiliadis, E. et al. "Clinical evaluation of a matrix metalloproteinase-12 cleaved fragment of titin as a cardiovascular serological biomarker" *Journal of Translational Medicine*, Jul. 6, 2012, pp. 1-10, vol. 10, No. 1.
Matsumura, K. et al. "Immunochemical study of connectin (titin) in neuromuscular diseases using a monoclonal antibody: connectin is degraded extensively in Duchenne muscular dystrophy" *Journal of the Neurological Sciences*, Nov. 1, 1989, pp. 147-156, vol. 93, No. 2-3.
Nadarajah, V. . et al. "Serum matrix metalloproteinase-9 (MMP-9) as a biomarker for monitoring disease progression in Duchenne muscular dystrophy (DMD)" *Neuromuscular Disorders*, May 27, 2011, pp. 569-578, vol. 21, No. 8.
Written Opinion in International Application No. PCT/FR2013/052280, dated Dec. 3, 2013, pp. 1-6.

* cited by examiner

*Primary Examiner* — Lisa V Cook
(74) *Attorney, Agent, or Firm* — Saliwanchik, Lloyd & Eisenschenk

(57) ABSTRACT

A method for the diagnosis, prognosis and therapeutic monitoring of muscular dystrophy, by detecting titin or one or more fragments of titin in a bodily fluid is provided.

9 Claims, 10 Drawing Sheets

Figure 1:
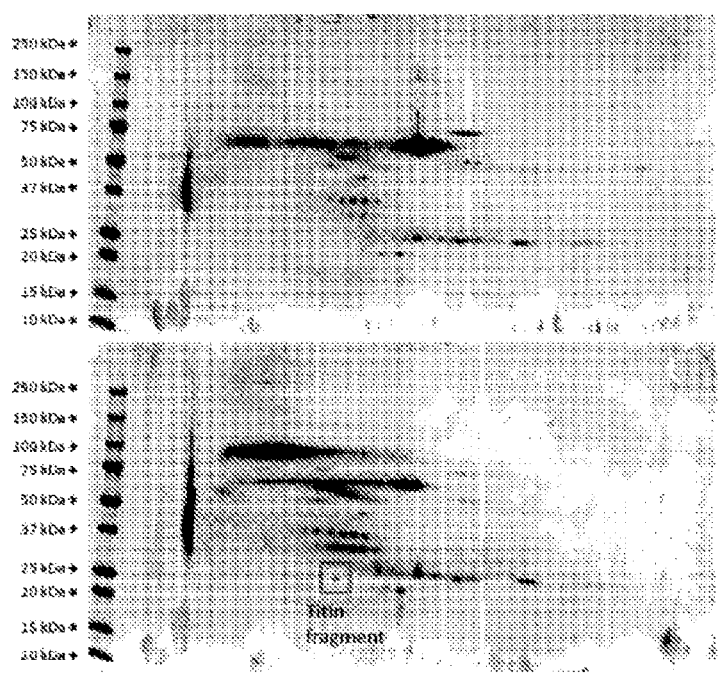

| Position of the peptide in the protein sequence | Peptide sequence (observed) | TG105745 (Gene approach Antibodies) | TG105745 (Gene approach Antibodies) | TG105745 (Gene approach Antibodies) | TG105745 (Gene approach Antibodies) |
|---|---|---|---|---|---|
| 42-62 | DGQVSTSTLPGVQ(S)FS CGR | | DGQVSTSTLPGVQS FSDGR | | |
| 82-98 | | ATNGSGQATSTAELL VK | ATNGSGQATSTAELV K | | ATNGSGQATSTAELL VK |
| 99-109 | AETAPPNPVQR | | AETAPPNPVQR | AETAPPNPVQR | |
| 110-116 | | | | LGSMYVR | |
| 127-136 | VTGIPTPVK | | VTGIPTPVK | | |
| 933-950 | | VPAPVEIPVTPPTLVS GLK | VPAPVEIPYTPPTLVS GLK | VPAPVEIPYTPPTLVS GLK | |
| 1004-1012 | | | | LAFAEDSGR | |
| 11784-11797 | | | | | KPEAPPKEPEPEK |
| 34245-34257 | | | DGGSPEGVTER | | |
| 34253-34271 | | | GPPKEALPSDISIDLG K | | |
| 34258-34271 | | IEALPSDISIDEGK | IEALPSDISIDEGK | | |
| 34272-34295 | | | VLTVACAFTSEPTPEV TWSCGGEK | | |

Figure 4

| Sequence | Location | IonScore DMD 1 | IonScore DMD 2 | IonScore DMD 3 | IonScore DMD 4 | IonScore DMD 5 |
|---|---|---|---|---|---|---|
| DGQVSTSTLPGVQJSFSDGR | 42-62 | 92 | 48 | 56 | 58 | 56 |
| ATNGSGQATSTAELLVK | 82-98 | 96 | 101 | 119 | 98 | 100 |
| AETAPPNFVQR | 99-109 | 51 | 50 | 58 | 60 | 58 |
| VTGIPTPVVK | 127-136 | 41 | 43 | 39 | 42 | 39 |
| ATSTAELLVQGEEEVPAK | 185-202 | 35 | 76 | 72 | 71 | 80 |
| VPAPVEIPVTPPTLVSGLK | 932-950 | 50 | 53 | 56 | 54 | 43 |
| TIKPPPVEPEPTPIAAPVTVPVVGK | 11958-11982 | 25 | 41 | 36 | 40 | 39 |
| DGVHDIPEDAQLETAENSSVIIPECK | 16783-16809 | 26 | 31 | 38 | 24 | 57 |
| FILNVQSKPTAEVK | 33320-33333 | 29 | 31 | 23 | 34 | 18 |
| NNLPTSISNVSISR | 34097-34111 | 61 | 65 | 69 | 55 | 75 |
| GIPPKIEALPSDISIDEGK | 34253-34271 | 30 | 54 | 39 | 66 | 84 |
| IEALPSDISIDEGK | 34258-34271 | 66 | 64 | 65 | 62 | 73 |
| VLTVACAFTGEPTPEVTWSCGGR | 34272-34294 | 72 | 53 | 52 | 60 | 50 |
| VLTVACAFTGEPTPEVTWSCGGRK | 34272-34295 | 49 | 57 | 60 | 63 | 71 |
| FHIENTDDLTTLIIMDVQK | 34304-34322 | 80 | 105 | 23 | 58 | 62 |

Figure 6

METHOD FOR DIAGNOSING MUSCULAR DYSTROPHY

CROSS-REFERENCE TO RELATED APPLICATION

This application is the U.S. national stage application of International Patent Application No. PCT/FR2013/052280, filed Sep. 26, 2013.

The Sequence Listing for this application is labeled "Seq-List.txt" which was created on Sep. 25, 2013 and is 2,908 KB. The entire contents of the sequence listing is incorporated herein by reference in its entirety.

FIELD OF THE INVENTION

The invention relates to a method for the diagnosis, prognosis and therapeutic monitoring of muscular dystrophy by detecting titin or one or more fragments of titin in a bodily fluid of a subject, preferably in urine or blood.

PRIOR ART

Duchenne muscular dystrophy (DMD) or Becker muscular dystrophy (BMD) are caused by mutations or deletions within the gene coding for dystrophin (Muntoni, Torelli et al. 2003). In the former case, in which the phenotype is more severe, dystrophin is totally absent. The DAPC (Dystrophin Associated Protein Complex), which enables connection between intracellular actin filaments and the extracellular matrix (Le Rumeur, Winder et al.), is also absent. This complex usually protects the membrane of muscle fibers which are subject to contractions and relaxations. In its absence, the fibers are no longer protected and degenerating muscle cells, and new cells which reflect regeneration tending to offset the phenomenon, are observed in the muscles (Batchelor and Winder 2006). Eventually, regeneration is insufficient and the fibers are replaced by adipose tissue.

From a therapeutic standpoint, there are currently high hopes for the exon skipping technique (Cirak, Arechavala-Gomeza et al.; Lu, Yokota et al.). Indeed, BMD, which leads to a less serious phenotype, is also due to one or more mutations within the gene coding for dystrophin, but the fundamental domains of the protein are retained:

- an N-terminal domain which binds to actin filaments, and
- a cysteine-rich C-terminal domain which binds to the DAPC.

For DMD patients, therefore, it is possible to obtain a Becker phenotype by excluding the exons which bear nonsense mutations within the messenger RNA (mRNA) and thus to re-establish the open reading frame. The protein produced, which is shorter, is then partially functional. This strategy is currently being tested in several clinical trials.

Regular multidisciplinary medical monitoring enables disease progression to be evaluated and the lives of patients to be improved through appropriate care. This involves preventing contractures, and providing technical aid, physiotherapy, cardiac monitoring, orthopedics and respiratory aid. Diagnostic monitoring is performed, among others, by evaluating motor functions, carrying out muscle biopsies, or assaying creatine kinase, an enzyme secreted into the circulation (Bushby, Finkel et al.).

Muscle biopsy analysis enables damaged fibers, smaller fibers reflecting muscle regeneration, and zones of necrosis replaced by adipose tissue to be observed. This method has the drawback of being highly invasive for the patient.

Another method consists of assaying creatine kinase (CK) in the blood. This enzyme is linked to energy metabolism present in several types of cells. An increase in the concentration thereof in the blood reflects the state of degradation of the muscle fibers. Nonetheless, this biomarker is not completely reliable since its level also depends on stress such as physical activity (Nicholson, Morgan et al. 1986). Moreover, its detection requires invasive methods (taking blood). Its level is generally measured after the presentation of the first clinical signs, around the age of 3. Progressive muscle degradation in DMD patients reduces the reliability of this marker with age.

Consequently, it appears necessary to identify new biomarkers which are more reliable for identifying muscular dystrophy and which could be assayed from samples taken non-invasively or only slightly invasively, such as taking urine, blood, serum or plasma samples.

The inventors were able to identify the presence, in the bodily fluids of patients suffering from muscular dystrophy, of a specific protein which is absent in the bodily fluids of healthy subjects. Implementation of this major breakthrough is the subject of the present invention.

SUMMARY OF THE INVENTION

The inventors studied samples of bodily fluids from patients suffering from muscular dystrophy so as to determine whether biomarkers specific for these diseases could be identified. This work enabled the presence of titin to be demonstrated in ill patients, in comparison to healthy donors.

Observing the presence of this marker in an ill individual in comparison to a healthy individual can be applied to the field of diagnostics. The present invention therefore relates to the use of titin or one or more fragments thereof to implement a method for the diagnosis of muscular dystrophy, in particular Duchenne muscular dystrophy. The method for the diagnosis, prognosis or monitoring of the efficacy of a treatment for muscular dystrophy in a subject notably comprises detecting the presence or absence of titin or one or more fragments of titin in a sample of bodily fluid from said subject. The presence of titin or a fragment of titin is indicative of muscular dystrophy, in particular Duchenne muscular dystrophy.

The invention also relates to a method for the diagnosis of muscular dystrophy, comprising determining the presence or quantity of titin or one or more fragments thereof in a biological sample from a subject, said biological sample being a sample of bodily fluid from said subject, notably a urine, blood, plasma, serum or saliva sample.

A higher level of titin or one or more fragments of titin in the sample taken from the tested subject in comparison to a healthy subject will indicate muscular dystrophy.

The presence of titin or one or more fragments thereof in a bodily fluid from patients suffering from muscular dystrophy, and in particular from DMD, has never been reported in prior publications.

The invention also relates to a method for monitoring the progression of (or a method for the prognosis of) muscular dystrophy, and a method for evaluating the efficacy of a therapeutic treatment for muscular dystrophy. In this case, the method comprises detecting titin or one or more fragments thereof in a second sample of bodily fluid from a subject, this level in the subject's sample being compared to the level of said titin or said one or more fragments in a first, reference sample which corresponds to a sample previously taken from the same subject. In the case of monitoring the efficacy of a treatment, the first sample may have been taken before administering the therapeutic treatment to the subject, and the second sample will be taken after administering the therapeutic treatment (for example several days/weeks/months after administering the therapeutic treatment). Alternatively, the first and second samples may both be taken after administering the therapeutic treatment (for example, the first sample is taken after treatment, on the same day as this treatment or several days/weeks/months after the treatment, and the second sample is taken several days/weeks/months after the first sample). Alternatively, the samples may be compared to "standard" samples from other patients with the same disease.

The invention also relates to a kit useful for the diagnosis of muscular dystrophy.

DETAILED DESCRIPTION OF THE INVENTION

Within the context of the invention, a "reference sample" or a "standard sample", when mention is made of a "healthy sample", corresponds to a sample of bodily fluid obtained from one or more subjects, preferably two or more, who do not suffer from muscular dystrophy. The reference sample may also correspond to a sample obtained from one or more patients suffering from muscular dystrophy. Within the context of methods for monitoring muscular dystrophy or for monitoring the efficacy of a treatment, the reference sample may notably be a sample taken from the subject to be monitored, but before the monitoring has begun.

The term "muscular dystrophy" notably denotes Duchenne muscular dystrophy, Becker muscular dystrophy and limb-girdle muscular dystrophies, such as α- and γ-sarcoglycanopathies. The invention relates more particularly to the study of Duchenne muscular dystrophy.

According to the invention, the biological sample from the subject being studied is a bodily fluid, notably a urine, blood, serum, plasma or saliva sample. According to a particular embodiment, the sample is a urine sample or a blood sample, more particularly a urine sample.

The term "subject" is understood to mean a human or non-human mammal, preferably a human mammal. The subject may be predisposed to muscular dystrophy (revealed for example by genetic testing or by a suspicion possibly arising from previous family history) or may suffer from manifested muscular dystrophy. The invention may also be used for screening, the subject not having any symptoms or known predisposition. In particular, the method according to the invention may be used for mass screening in young children or in newborns. The invention may also be used for prenatal diagnosis of muscular dystrophy. The invention may also be used in monitoring animal models, including canine models, notably GRMD (Golden Retriever Muscular Dystrophy) dogs, and murine models, notably mdx mice, during preclinical treatment development.

The inventors have notably demonstrated that titin or one or more fragments thereof is particularly useful for detecting or monitoring dystrophy in early childhood, since it can be detected at least from the age of 3, and probably earlier. Thus, according to a particular embodiment, the subject is an adult, an adolescent or a child, notably a child less than 10 years old, less than 5 years old, or less than 4 years old, or the subject is a child who is 3 years old or less than 3 years old, or the subject is a newborn. As a result, the disease can be detected at a very early stage.

The invention is also aimed at a method for the diagnosis of muscular dystrophy, comprising detecting the presence or absence of titin or a fragment of titin in a sample of bodily fluid from a subject, the presence of said titin or said fragment being indicative of muscular dystrophy.

The invention is notably aimed at detecting titin in a urine sample from a subject. At the current time, there are no means for diagnosing muscular dystrophy from urine.

One approach which may enable the early diagnosis of these diseases in a large number of patients will enable candidates to be identified for diagnosis by sequencing. Likewise, the sooner the screening can be carried out, the more effective gene therapy treatment will be, compensating for muscle lysis and depletion of muscle cell reserves.

Thus, according to one embodiment, the present invention relates to a method for the early diagnosis of muscular dystrophy, in particular Duchenne muscular dystrophy.

Titin (TITIN HUMAN, UniProt Knowledgebase number: Q8WZ42) is the largest protein (38138 residues; MW 3.8 MDa) of the proteins encoded by the human genome, and contributes to sarcomere organization. This protein is important for the assembly and stability of the sarcomere and its organization has various types of modules and multiple zones of contact with sarcomere proteins. In vertebrate cardiac and skeletal muscles, each titin molecule adheres to the thick myosin filaments over almost its entire length and contributes to the elasticity of each half-sarcomere from the M-line to the Z-line. The mutations found on titin are responsible for a large number of muscle diseases: dilated cardiomyopathies (CMD1G); a type of limb-girdle dystrophy (LGMD2J); and EOMFC (early-onset myopathy with fatal cardiomyopathy).

Eleven isoforms of titin produced by alternative splicing have been identified, from Q8WZ42-1 to Q8WZ42-11:

Isoform 1 (Identifier: Q8WZ42-1; SEQ ID NO:1)—Canonical sequence;

Isoform 2 (Identifier: Q8WZ42-2; SEQ ID NO:2)—The sequence of this isoform differs from the canonical sequence as follows: 555-646: Missing;

Isoform 3 (Identifier: Q8WZ42-3; SEQ ID NO:3)—Also known as: Small cardiac N2-B; the sequence of this isoform differs from the canonical sequence as follows: 556-601: Missing; 4474-11851: Missing;

Isoform 4 (Identifier: Q8WZ42-4; SEQ ID NO:4)—Also known as: Soleus; the sequence of this isoform differs from the canonical sequence as follows: 3454-4380: Missing; 11507-11507: E→EVFEEPEESPSAPPKKPEVPPVR;

Isoform 5 (Identifier: Q8WZ42-5; SEQ ID NO:5)—The sequence of this isoform differs from the canonical sequence as follows: 10382-10645: Missing; 10742-10931: Missing; 11015-11163: Missing; 11223-11852: Missing; 11985-12201: Missing;

Isoform 6 (Identifier: Q8WZ42-6; SEQ ID NO:6)—Also known as: Small cardiac novex-3; the sequence of this isoform differs from the canonical sequence as follows: 3455-5604: FSSSFLSAEE . . . VLDLIIPPSF→LFSEGESEHS . . . AESFAALTLT; 5605-34350: Missing;

Isoform 7 (Identifier: Q8WZ42-7; SEQ ID NO: 7)—Also known as: Cardiac novex-2; the sequence of this isoform differs from the canonical sequence as follows: 3435-3645: APESILHERI . . . LPAIFEYTVV→VQALDRQSSG . . . IEQEIEMEMK; 3646-4380: Missing;

Isoform 8 (Identifier: Q8WZ42-8; SEQ ID NO:8)—Also known as: Cardiac novex-1; the sequence of this isoform differs from the canonical sequence as follows: 3434-3434; E→EGFSKFEENT . . . CAATLTVTPK;

Isoform 9 (Identifier: Q8WZ42-9; SEQ ID NO:9)—The sequence of this isoform differs from the canonical sequence as follows: 556-601: Missing; 3434-3434: E→EVQALDRQSS . . . TTSAVLSVEG; 4474-11851: Missing;

Isoform 10 (Identifier: Q8WZ42-10; SEQ ID NO:10)—The sequence of this isoform differs from the canonical sequence as follows: 556-601: Missing; 3434-3434: E→EGFSKFEENT . . . CAATLTVTPK; 4474-11851: Missing; and Isoform 11 (Identifier: Q8WZ42-11; SEQ ID NO:11)—The sequence of this isoform differs from the canonical sequence as follows: 3454-4380: Missing.

The central portion of titin varies according to the isoforms, but the first 556 amino acids are the same in these isoforms.

The sequence of titin is highly conserved; for example, there is 89.4% homology between the human protein and the mouse protein (TITIN Mouse, UniProtKB Knowledgebase number: A2ASS6).

According to a particular embodiment, the titin fragments detected include fragments containing the peptides shown in the table of FIG. 4 or FIG. 6 or FIG. 10B. Thus, by way of illustration, the fragments detected according to the invention comprise titin fragments comprising amino acids 42-62 (SEQ ID NO:12), 82-98 (SEQ ID NO:13), 99-109 (SEQ ID NO:14), 110-116 (SEQ ID NO:15), 127-136 (SEQ ID NO:16), 932-950 (SEQ ID NO:17), 1004-1012 (SEQ ID NO:18), 11784-11797 (SEQ ID NO:19), 14245-14257 (SEQ ID NO:20), 34253-34271 (SEQ ID NO:21), 34258-34271 (SEQ ID NO:22), 34272-34295 (SEQ ID NO:23), 185-202 (SEQ ID NO:24), 11958-11982 (SEQ ID NO:25), 16783-16809 (SEQ ID NO:26), 33320-33333 (SEQ ID NO:27), 34097-34111 (SEQ ID NO:28), 34272-34294 (SEQ ID NO:29) and/or 34304-34322 (SEQ ID NO:30). According to another embodiment, the fragments according to the invention are fragments corresponding to the N-terminal part of titin, notably comprising the first 300 amino acids of the protein. According to another embodiment, the fragments according to the invention are fragments corresponding to the C-terminal part of titin, notably comprising the last 150 amino acids of the protein. According to another embodiment, the fragments according to the invention are intermediate fragments between the N-terminal and C-terminal parts of titin, notably a fragment between amino acids 12132 and 15880 of SEQ ID NO:1. For example, the fragment detected may comprise, in the mouse titin sequence, amino acids 12994-13002 (SEQ ID NO:31), 13352-13362 (SEQ ID NO:32), 13542-13558 (SEQ ID NO:33), 14512-14524 (SEQ ID NO:34), 14867-14883 (SEQ ID NO:35), 14975-14993 (SEQ ID NO:36), 15034-15053 (SEQ ID NO:37), 15203-15214 (SEQ ID NO:38), 15234-15248 (SEQ ID NO:39), 15636-15645 (SEQ ID NO:40), 15746-15759 (SEQ ID NO:41), 15968-15987 (SEQ ID NO:42), 16034-16048 (SEQ ID NO:43), 16133-16148 (SEQ ID NO:44) and/or 16432-16442 (SEQ ID NO:45). The invention also comprises detecting titin fragments corresponding to the positions of amino acids of the sequences SEQ ID NO:31 to SEQ ID NO:45 in the human titin sequence.

According to a particular embodiment, the method according to the invention comprises detecting or measuring the level of at least one of the sequences SEQ ID NO:1 to SEQ ID NO:45, or a sequence which is at least 90%, in particular at least 95%, more particularly at least 98% or at least 99% identical to one of the sequences SEQ ID NO:1 to SEQ ID NO:45.

The presence of titin or a fragment of titin may be detected by any conventional method, such as:
ELISA (enzyme-linked immunosorbent assay),
Western blotting,
mass spectrometry, or
any other method enabling specific detection of a protein.

In particular, the ELISA and Western blotting techniques are well known to those skilled in the art and implement the use of specific antibodies for the protein to be detected. Any antibody capable of specifically binding titin, one or more fragments thereof, and more particularly an N-terminal or C-terminal titin fragment, notably comprising approximately the 300 N-terminal amino acids or the 150 C-terminal amino acids of titin, can be used within the context of the present invention. This includes polyclonal or monoclonal antibodies which recognize titin or an epitope thereof, and in particular polyclonal or monoclonal antibodies specific for the N-terminal part or the C-terminal part of titin. Those skilled in the art are able to produce antibodies specific for a protein, such as titin or one of the fragments thereof, on the basis of their general knowledge. Moreover, several commercial antibodies are available, notably directed against the N-terminal part of titin. By way of illustration, it is possible to use the mouse anti-titin monoclonal IgG (#H00007273-M07 clone 2F12, from Abnova) used in the examples below. It is also possible to use the diluted rabbit anti-titin monoclonal IgG used in the examples below directed against the C-terminal part (recognizing the sequence: NEFGSDSAT-VNINIRSMC (SEQ ID NO:46); amino acids 35197 to 35213 in the mouse corresponding to amino acids 34334 to 34349 in humans).

Similarly, the mass spectrometry technique is well known to those skilled in the art, and consists of identifying proteins by measuring the mass-to-charge ratios (m/z) of the peptides obtained from enzymatic digestion (MS) or fragments of said peptides (MS/MS). The masses of the peptides generated are then compared to those of protein sequences present in databases, enabling identification of the protein. The identification of one or more titin peptides, and more particularly a peptide obtained from an N-terminal or C-terminal titin fragment, comprising notably approximately the 300 N-terminal amino acids or the 150 C-terminal amino acids of titin, can be used in the context of the present invention. According to a particular embodiment, the MRM (multiple reaction monitoring) mode is used to enable quantitative and/or qualitative detection of the peptides through the entire protein.

According to another aspect, the invention relates to a method for monitoring muscular dystrophy as described above. In this case, the method comprises quantifying the level of titin or one or more fragments of titin at a time T1 in the subject being studied, higher expression of said titin or said fragment(s) of titin at a time T2, after T1, being indicative of progression of the dystrophy, and the same expression or lower expression of said titin or said fragment(s) of titin at a time T2, after T1, being respectively indicative of stabilization or remission. This change in the level of titin may also be compared to a standard sample from a patient of corresponding age suffering from muscular dystrophy.

According to another aspect, the invention relates to a method for monitoring the efficacy of a treatment for muscular dystrophy. In this case, the method comprises quantifying the level of titin or a fragment or fragments of titin at a time T1 in the subject being studied, lower expression of said titin or said fragment(s) of titin at a time T2, after T1, being indicative of effective treatment of the dystrophy. Alternatively, the level of titin or one or more fragments thereof at a time T is compared to the level detected in a standard sample from a patient suffering from muscular dystrophy. A lower level in the subject being studied will be indicative of effective treatment of the dystrophy.

The terms "higher level of expression" or "lower level of expression" are understood to mean a level of expression, the variation in which is significant, according to procedures well-known to those skilled in the art.

Of course, in the two monitoring methods described above, a method for assaying titin or one or more fragments thereof is used, notably an ELISA or MRM mass spectrometry assay.

According to the methods for monitoring the progression of dystrophy and monitoring the efficacy of a treatment, the first sample and the second sample of bodily fluid are taken in a manner staggered over time (for example several days/weeks/months after administering the therapeutic treatment). Moreover, in the case of monitoring the efficacy of a treatment, the first and second samples may both be taken after administering the therapeutic treatment (for example, the first sample is taken after treatment, on the same day as the treatment or several days/weeks/months after the treatment, and the second sample is taken several days/weeks/months after the first sample).

The diagnosis of the disease or the monitoring of the progression of the disease or the efficacy of the treatment may moreover be confirmed in procedures following the methods according to the invention, comprising known steps for evaluating muscular dystrophy (for example, determining the level of creatine kinase, looking for specific markers in muscle biopsies, etc.).

The invention also relates to a kit for diagnosing muscular dystrophy, this kit comprising the means for detecting or assaying titin or a fragment thereof. In a particular embodiment, the diagnostic kit is a kit comprising the means for carrying out an ELISA or Western blot test. To this end, the diagnostic kit contains a means for detecting titin or one or more fragments thereof, notably an N-terminal or C-terminal titin fragment, the detecting means corresponding notably to one or more polyclonal or monoclonal antibodies. The kit may also comprise instructions to follow for implementing the method according to the invention.

The present invention is illustrated by the following figures and examples.

LEGEND OF THE FIGURES

FIG. 1. Identification by two-dimensional electrophoresis of an N-terminal titin fragment in DMD urine.

Figure 2:
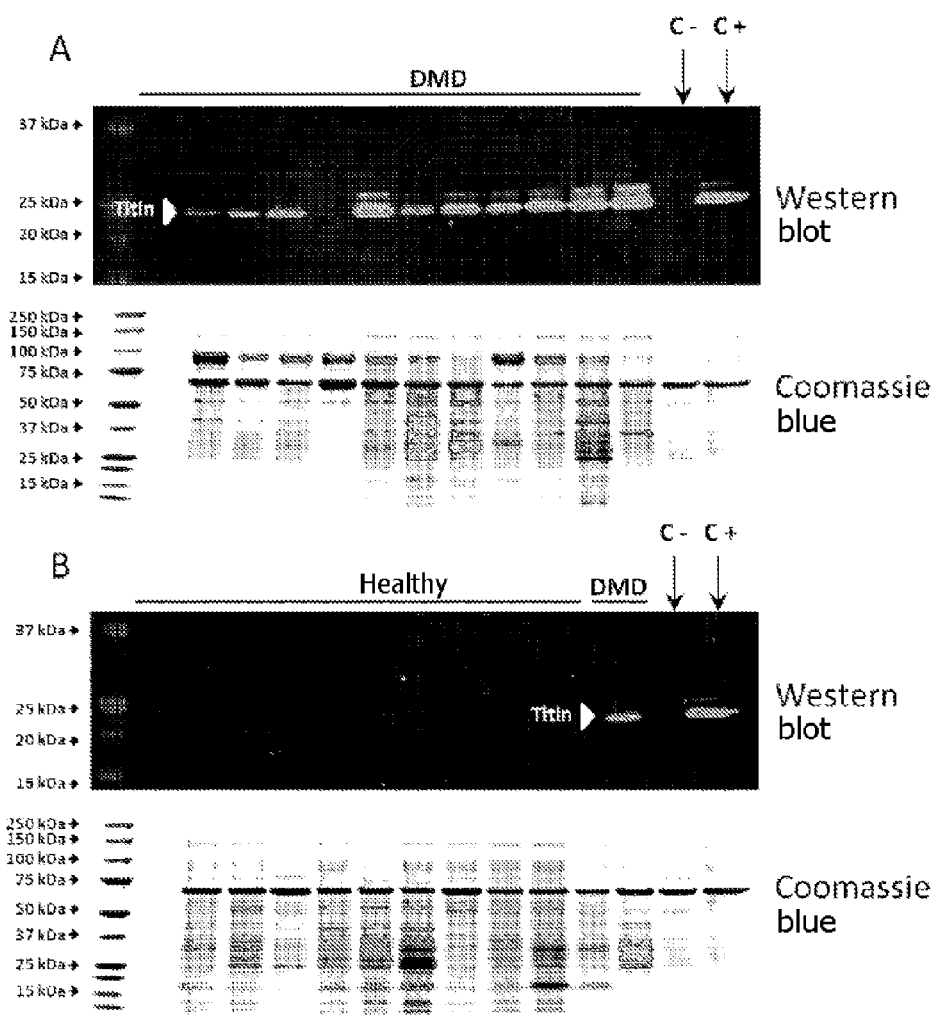

FIG. 2. Western blot analysis of the presence of the N-terminal titin fragment in urine from DMD and healthy patients.

Figure 3:
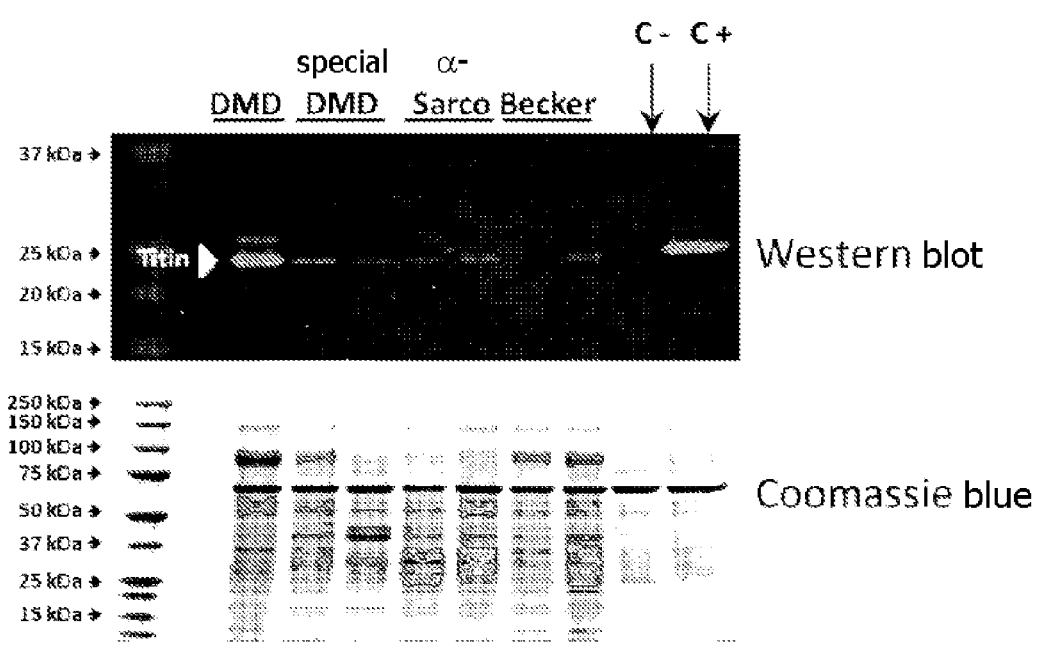

FIG. 3. Western blot analysis of the presence of the N-terminal titin fragment in urine from other muscular dystrophies.

FIG. 4. Detection of peptides from the various parts of titin in urine from DMD patients, using "two-dimensional electrophoresis" and "LC-MS/MS" approaches. Position of the peptides in the titin sequence and the corresponding sequence identifier are as follows: 42-62 (SEQ ID NO:12), 82-98 (SEQ ID NO:13), 99-109 (SEQ ID NO:14), 110-116 (SEQ ID NO:15), 127-136 (SEQ ID NO:16), 932-950 (SEQ ID NO:17), 1004-1012 (SEQ ID NO:18), 11784-11797 (SEQ ID NO:19), 14245-14257 (SEQ ID NO:20), 34253-34271 (SEQ ID NO:21), 34258-34271 (SEQ ID NO:22) and 34272-34295 (SEQ ID NO:23).

Figure 5:
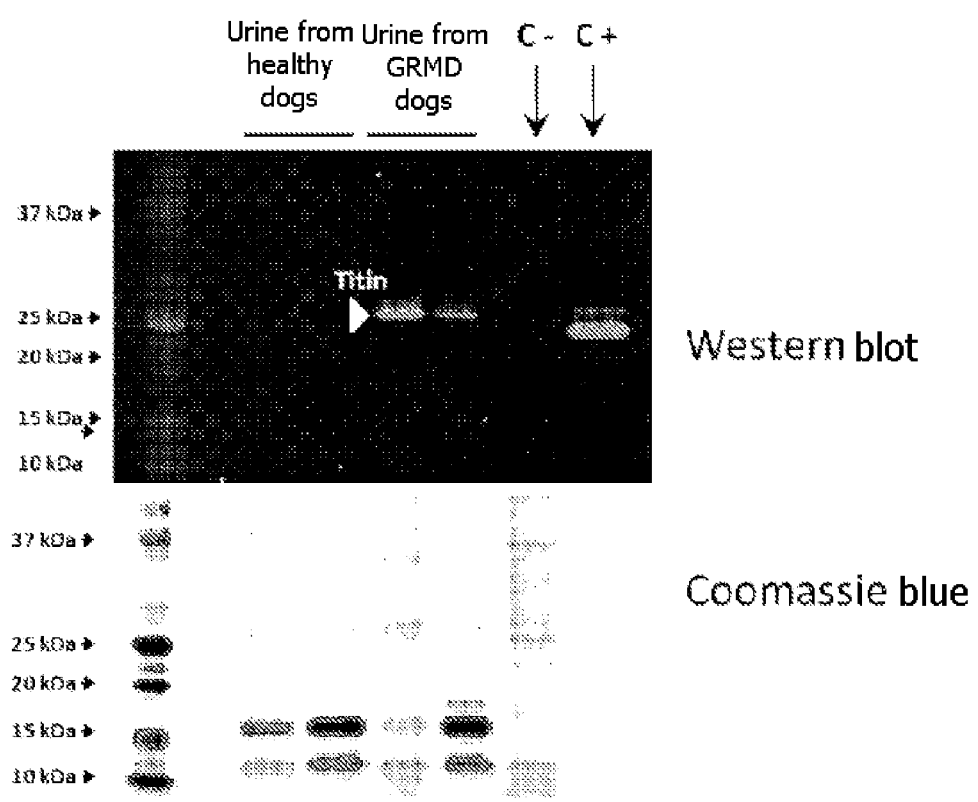

FIG. 5. Western blot analysis of the presence of the N-terminal titin fragment in urine from GRMD and healthy dogs.

FIG. 6. Detection of peptides from the various parts of titin in urine from DMD patients, using "LC-MS/MS" approaches. Position of the peptides in the titin sequence and the corresponding sequence identifier are as follows: 42-62 (SEQ ID NO:12), 82-98 (SEQ ID NO:13), 99-109 (SEQ ID NO:14), 127-136 (SEQ ID NO:16), 185-202 (SEQ ID NO:24), 932-950 (SEQ ID NO: 24), 11958-11982 (SEQ ID NO:25), 16783-16809 (SEQ ID NO:26), 33320-33333 (SEQ ID NO:27), 34097-34111 (SEQ ID NO:28), 34253-34271 (SEQ ID NO:21), 34258-34271 (SEQ ID NO:22), 34272-34294 (SEQ ID NO:29), 34272-34295 (SEQ ID NO:23) and 34304-34322 (SEQ ID NO:30).

Figure 7:
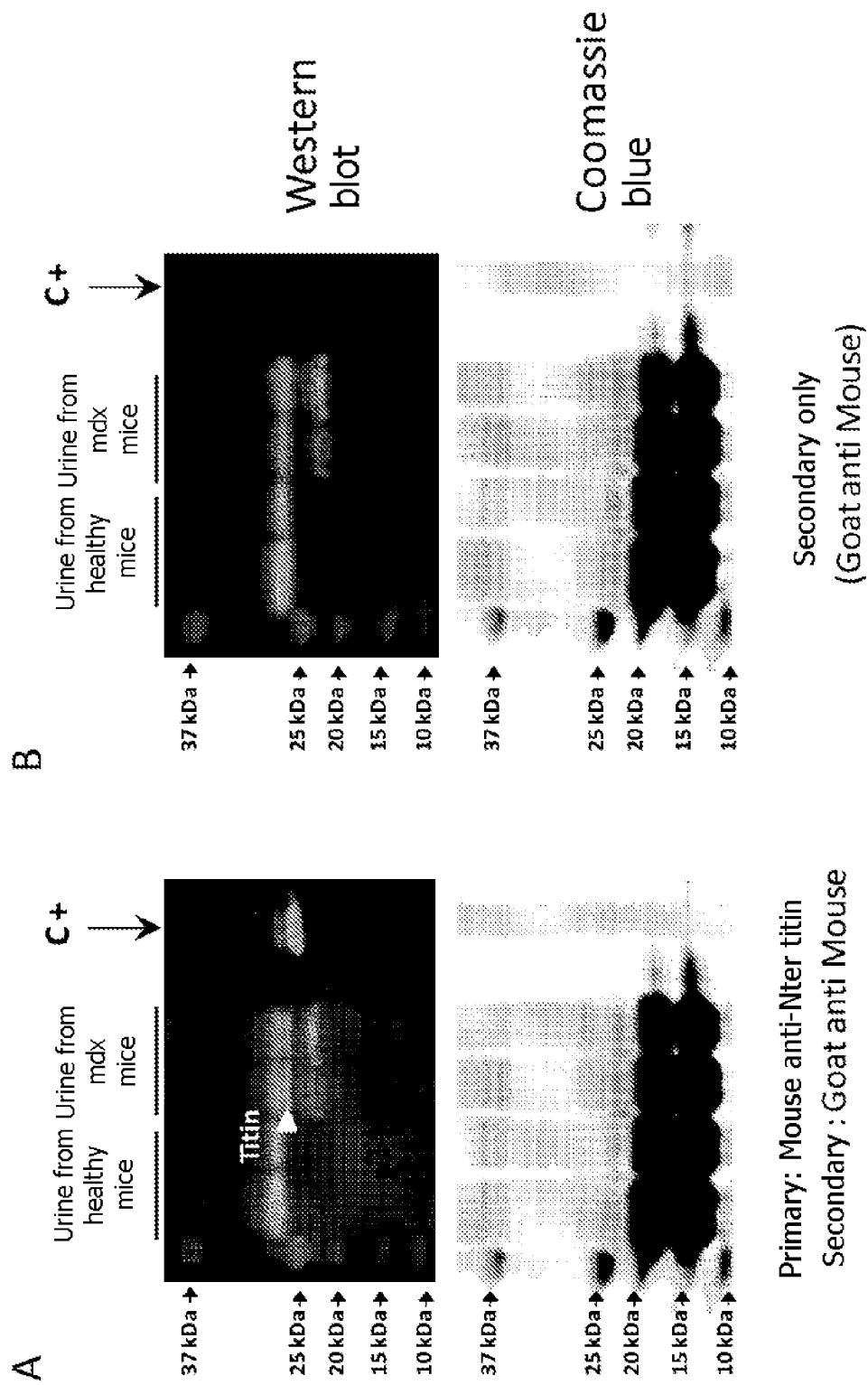

FIG. 7. Western blot analysis of the presence of the N-terminal titin fragment in urine from mdx and healthy mice.

Figure 8:
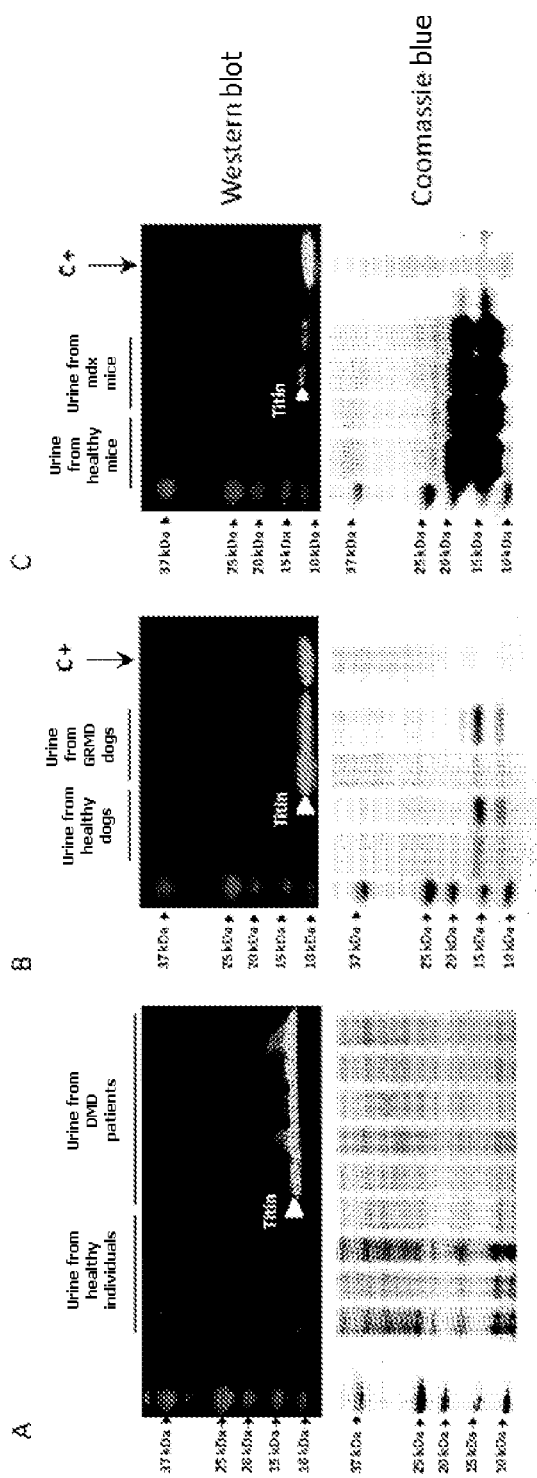

FIG. 8. Western blot analysis of the presence of the C-terminal titin fragment in urine from DMD patients, GRMD dogs and mdx mice and their respective healthy controls.

Figure 9:
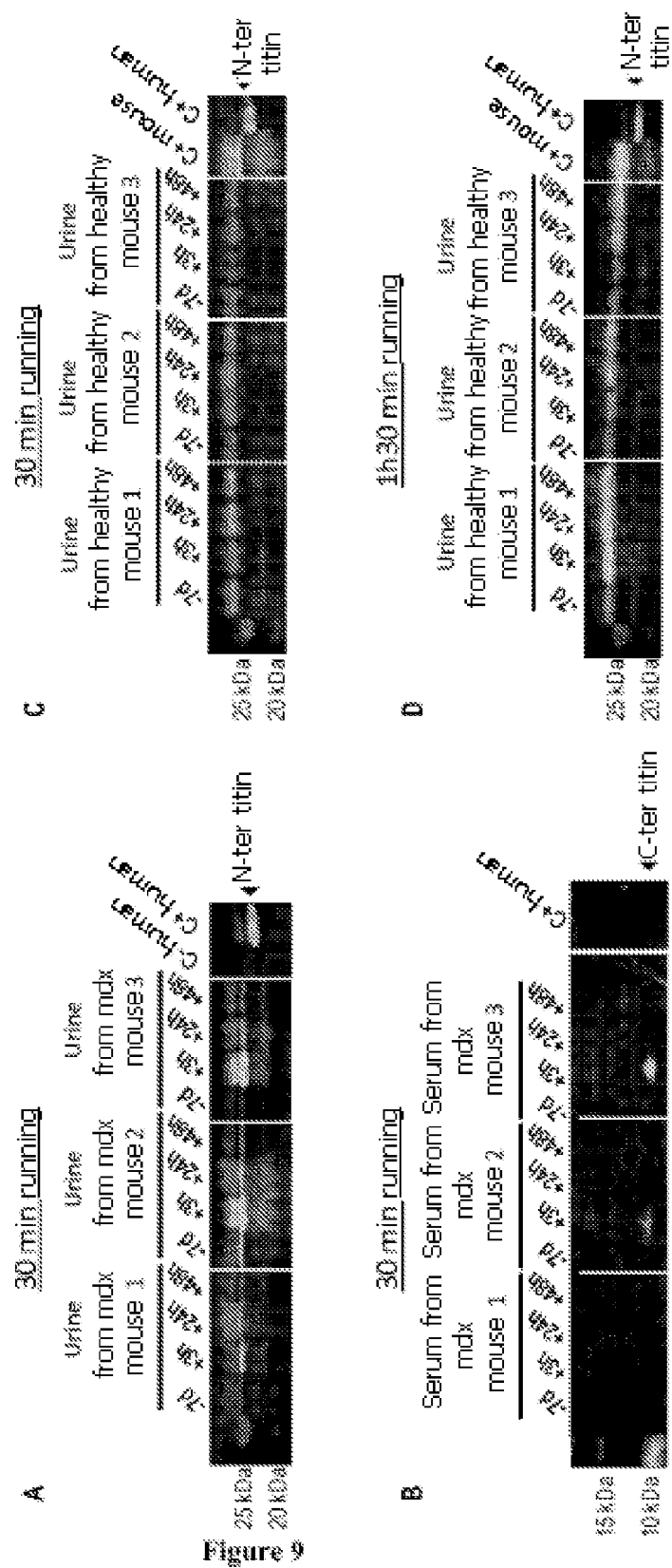

FIG. 9. Western blot analysis of the presence of the N-terminal or C-terminal titin fragment in urine and sera from mdx and healthy mice having undergone physical exercise.

Figure 10:
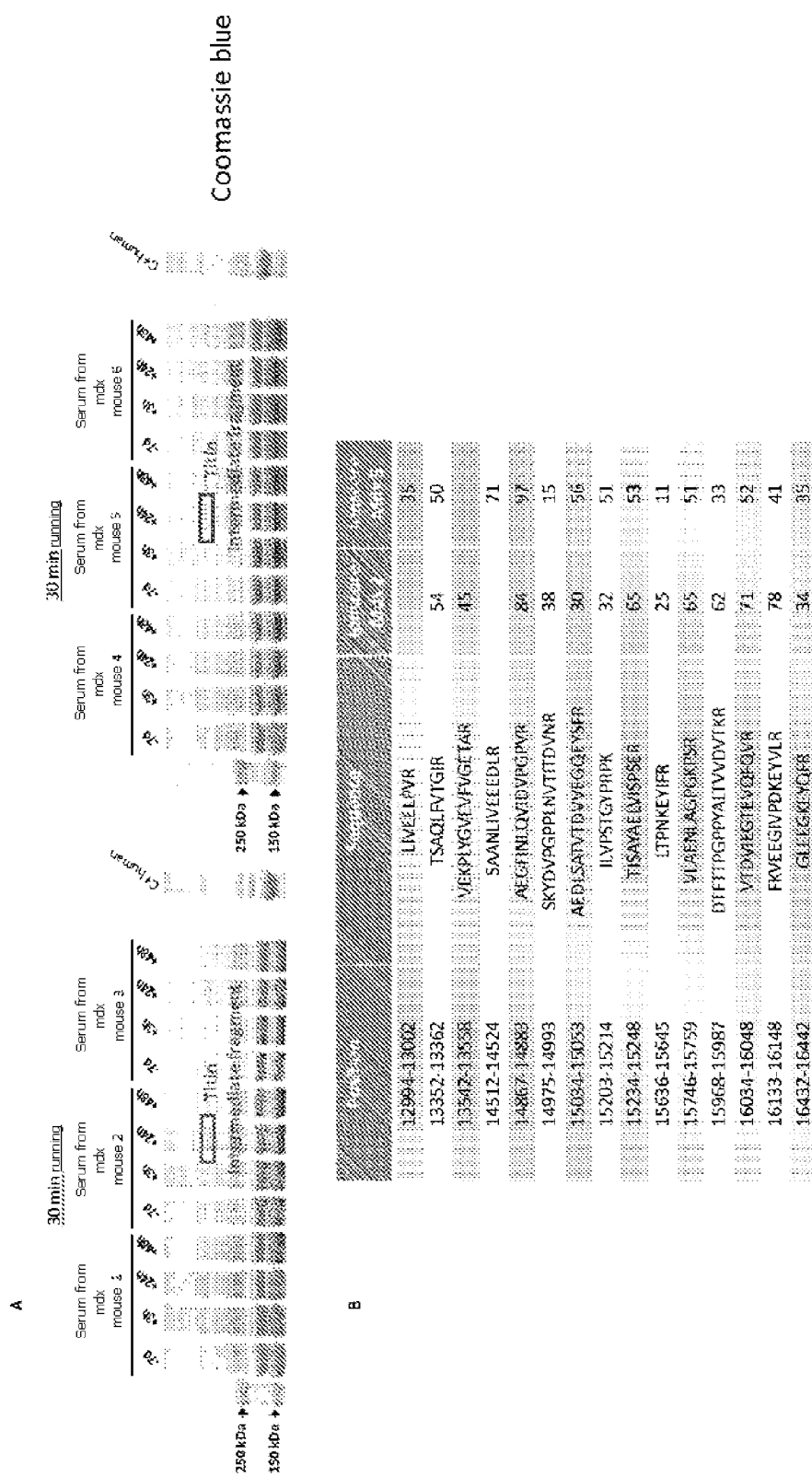

FIG. 10. Identification, using the "MALDI-TOF/TOF" approach, of an intermediate titin fragment in sera from mdx mice having undergone physical exercise. Position of the peptides in the titin sequence and the corresponding sequence identifier are as follows: 12994-13002 (SEQ ID NO:31), 13352-13362 (SEQ ID NO:32), 13542-13558 (SEQ ID NO:33), 14512-14524 (SEQ ID NO:34), 14867-14883 (SEQ ID NO:35), 14975-14993 (SEQ ID NO:36), 15034-15053 (SEQ ID NO:37), 15203-15214 (SEQ ID NO:38), 15234-15248 (SEQ ID NO:39), 15636-15645 (SEQ ID NO:40), 15746-15759 (SEQ ID NO:41), 15968-15987 (SEQ ID NO:42), 16034-16048 (SEQ ID NO:43), 16133-16148 (SEQ ID NO:44) and 16432-16442 (SEQ ID NO:45).

EXAMPLES

Materials and Methods

Protein Analysis by Two-Dimensional Electrophoresis

Proteins obtained from the urine of three DMD patients and three healthy subjects were compared by two-dimensional electrophoresis. Isoelectric focusing was carried out on an immobilized pH gradient gel (IPG Strip pH 3-10, Bio-Rad, referred to as the "strip"). Passive rehydration of the gel was carried out in the presence of the sample solubilized in denaturing buffer (7 M urea, 2 M thiourea, 20 mM DTT, 2% CHAPS, 1% ASB-14, 1% TRITON). Migration was carried out according to the following program: 50 V for 5 h, linear increase to 4000 V over the course of 6 h, then 8000 V for a total of 30,000 Vh. The strip was then equilibrated with 3 ml of buffer (0.375 M Tris-HCl, pH 8.8, 6 M urea, 20% glycerol, 2% SDS, 20 mM DTT) for 10 minutes. The equilibration step was repeated twice. For the second dimension, the strips were transferred to a linear gradient acrylamide gel (Criterion TGX 4-20% Precast Gel, Bio-Rad). Electrophoresis was carried out at 50 V for 30 minutes, then 140 V for 1 h 30 in 1×TGS buffer (25 mM Tris, 192 mM glycine, 0.1% SDS). The proteins were then stained for 1 hour in a Coomassie blue solution (InstantBlue, Expedeon) and destained by means of successive water baths.

Identification by MALDI-TOF/TOF Mass Spectrometry of the Proteins Separated by Two-Dimensional Electrophoresis Digestion of the Proteins Separated by Two-Dimensional Electrophoresis The spots of interest were extracted manually and placed in 1.5 ml Eppendorf tubes. They were washed successively with 500 μl of ethanol for 10 minutes, 500 μl of water for 5 minutes and 500 μl of ethanol for 10 minutes. After removal of the ethanol, digestion was carried out overnight at 37° C. in the presence of 30 ng of porcine trypsin (Promega) per spot in 10 μl of $NH_4CO_3$ buffer, pH 7.9. The peptides were desalted/concentrated on ZipTip μC18 tips (Millipore) then washed with 1% formic acid. They were then eluted in 1 μl of solution containing 3 mg/ml α-cyano-4-hydroxycinnamic acid (CHCA) matrix, 80% acetonitrile and 1% formic acid in order to be analyzed by MALDI-TOF/TOF mass spectrometry.

MALDI-TOF/TOF Mass Spectrometry Analysis

The system used is a MALDI-TOF/TOF ABI 4800+ system (Applied Biosystems, Foster City, Calif.) coupled with a 200 Hz YAG laser (355 nm). The spectra were acquired and the data processed using the 4000 Series Explorer software (version 3.5.1, Applied Biosystems). All the MS and MS/MS spectra were submitted to an in-house Mascot server (Matrix Science, Boston, Mass.) using the Swiss-Prot database. The mass tolerance of the fragment ions was fixed at 100 ppm for the precursor ions and 0.3 daltons for the fragment ions.

Identification of Total Proteins by LC-MS/MS Mass Spectrometry

Digestion of the Proteins in Solution

All the urine or blood (serum) proteins underwent enzymatic digestion followed by LC-MS/MS analysis. Protein digestion was carried out with two enzymes successively: endoproteinase Lys-C and trypsin. For this purpose, 50 μg of proteins were solubilized in a 50 μl reaction volume containing 50 mM Tris-HCl, pH 8.3, 6 M urea and 2 M thiourea. The proteins were reduced with 1 μl of 500 mM DTT (final concentration: 10 mM) at room temperature for 30 minutes. Then the proteins were alkylated with 6 μl of 550 mM iodoacetamide (final concentration: 55 mM) for 20 minutes. The proteins were digested with 5 μl of endoproteinase Lys-C (1 μg) for 3 hours at room temperature in darkness. The mixture was diluted 4 times with 3 volumes of MQ water (195 μl for a final volume of 260 μl; final concentration of urea/thiourea: 1.5 M/0.5 M) and the proteins were digested by 10 μl of trypsin (1 μg) for 16 hours at room temperature in darkness. Digestion was ended by adding 8.4 μl of 100% formic acid (final concentration: 3%).

LC-MS/MS Mass Spectrometry Analysis

The peptides were analyzed by liquid chromatography coupled to a tandem mass spectrometer (LC-MS/MS). The system used was an LTQ Orbitrap Velos mass spectrometer (Thermo Fisher Scientific, San Jose, Calif.) coupled to an Easy nano-LC Proxeon chromatography system (Thermo Fisher Scientific, San Jose, Calif.). The peptides in solution were desalted/concentrated in ZipTip μC18 tips (Millipore), then washed with 1% formic acid. They were then eluted by a 50% acetonitrile and 0.1% formic acid solution, dried, then taken up again in 0.1% formic acid. Chromatographic separation of the peptides was carried out with the following parameters: C18 Proxeon Easy Column (10 cm, 75 μm i.d, 120 Å), with a flow rate of 300 nl/min progressing from 95% solvent A (water—0.1% formic acid) to 25% solvent B (100% acetonitrile, 0.1% formic acid) in 20 minutes, then to 45% B in 40 min and finally to 80% B in 10 min. The peptides were analyzed in the Orbitrap in full ion scan mode with a resolution of 30,000 and a mass range from 300 to 2000 m/z. The fragments (CID) were obtained by collision-induced dissociation (CID) with a collision activation energy of 40% and were analyzed in the LTQ. The MS/MS data were acquired in a mode in which the 20 most intense precursor ions were isolated, with a dynamic exclusion of 15 seconds. The data were processed with the Proteome Discoverer 1.3 software (Thermo Fisher Scientific, San Jose, Calif.) coupled to an in-house Mascot search server (Matrix Science, Boston, Mass.; version 2.3.2). The mass tolerance of the fragment ions was fixed at 10 ppm for the precursor ions and 0.6 daltons for the fragments. Oxidation (M) and carbamidomethylation (C) were considered as possible variable modifications. The maximum number of cleavage errors was limited to two for trypsin digestion. The MS-MS data were analyzed with reference to the Swiss-Prot database.

Western Blot Protein Analysis

The samples of interest were loaded on a 1D SDS-PAGE 4-12% Bis-tris gel (Invitrogen), and migration was carried out for 30 minutes at 50 volts, then 1 hour 40 at 140 volts in 1×MOPS buffer (Invitrogen). Then the proteins were transferred onto a PVDF membrane (Millipore) for 2 hours at 40 volts. The membrane was saturated in Odyssey buffer (LI-COR Biosciences) overnight at 4° C. and incubated with the primary antibody for 1 hour at room temperature with agitation, followed by three 10-minute washes with PBS-0.1% TWEEN. Visualizing was carried out by incubating the membrane with a secondary antibody, labeled with a fluorophore emitting in the infrared range at 800 nm, for 1 hour at room temperature with agitation, away from light, followed by three 10-minute PBS-0.1% TWEEN washes, then 2 PBS washes. The fluorescent signal was revealed by scanning the membrane with the Odyssey imager (LI-COR Biosciences).

Primary antibody (1): Mouse anti-titin monoclonal IgG at a concentration of 1 μg/ml (#H00007273-M07 clone 2F12, from Abnova, directed against the N-terminal part (amino acids 1 to 111))

Primary antibody (2): Rabbit anti-titin monoclonal IgG diluted to 1/300th directed against the C-terminal part (sequence: NEFGSDSATVNINIRSMC SEQ ID NO: 46); amino acids 35197 to 35213 in the mouse corresponding to amino acids 34334 to 34349 in humans) (Charton et al., 2010)

Secondary antibody (1): Goat anti-mouse polyclonal antibody at a concentration of 0.1 μg/ml (IRDye 800CW Goat anti-mouse, LI-COR Biosciences)

Secondary antibody (2): Goat anti-rabbit polyclonal antibody at a concentration of 0.1 μg/ml (IRDye 800CW Goat anti-rabbit, LI-COR Biosciences)

Physical Exercise in Mice

Two groups of 6 male mice (healthy and mdx) were placed on a treadmill inclined downwards (15°) so as to perform a session of running for 30 minutes (8 m/min for 5 minutes, then 12 m/min for 25 minutes). The urine and sera of the mice were collected 7 days before exercise and also 3 h, 24 h and 48 h after exercise.

Moreover, since the mdx mice could not perform physical exercise lasting longer than 30 mins, a group of 6 healthy male mice underwent the same exercise but for 1 h 30 (8 m/min for 5 minutes, then 12 m/min for 1 h 25 minutes). The urine and sera of the mice were collected 7 days before exercise and also 3 h, 24 h and 48 h after exercise.

Results

The proteins were separated as described in Materials and Methods. FIG. 1 corresponds to a representative gel from the experiment. The top gel shows the results from separating the proteins from a healthy subject, and the bottom gel the proteins from a DMD individual. The framed spot was identified by MALDI-TOF/TOF mass spectrometry as an N-terminal titin fragment. This fragment was only detected in the urine from DMD patients. The results are representative for three different DMD patients and three different healthy subjects.

The proteins were analyzed by Western blot as described in Materials and Methods. FIG. 2 corresponds to a representative result in which panel (A) corresponds to the results from the analysis of the DMD patients and (B) the results from the healthy subjects. The N-terminal titin fragment (marked as "Titin" on the Western blot) was detected in 11 out of 12 DMD patients, and was undetectable in the 10 healthy subjects analyzed. C− negative control: urine from the healthy subject previously analyzed by two-dimensional electrophoresis; C+ positive control: urine from the DMD patient analyzed by two-dimensional electrophoresis.

In total, 23 DMD patients were tested using this method and the N-terminal titin fragment was detected in 21 of them. This fragment was absent in the urine from healthy individuals (13 subjects tested).

The proteins were analyzed by Western blot as described in Materials and Methods. FIG. 3 shows the results from the analysis of urine from patients suffering from the following muscular dystrophies: Duchenne muscular dystrophy (DMD); a distinctive case of DMD (patient walking at the age of 21) (special DMD); α-sarcoglycanopathy (α-Sarco); and Becker muscular dystrophy (Becker). The N-terminal titin fragment (marked as "Titin" on the Western blot) was detected in the distinctive case of DMD, in those patients suffering from α-sarcoglycanopathy (2 out of 2) and in one patient suffering from Becker muscular dystrophy (1 out of 2). C− negative control: urine sample from the healthy subject analyzed by two-dimensional electrophoresis; C+ positive control: urine sample from the DMD patient analyzed by two-dimensional electrophoresis.

The peptides obtained from the digestion of proteins from urine or blood of DMD patients and healthy patients were analyzed by the "two-dimensional electrophoresis" and "LC-MS/MS" approaches as described in Materials and Methods. The peptides sequenced by MS/MS are shown in FIG. 4. By means of the "two-dimensional electrophoresis" approach, the three peptides of the N-terminal part of titin were identified in the three DMD patients. A pool of 13 urine samples from DMD patients was also analyzed by the "LC-MS/MS" approach (three different analyses). The same peptides from the N-terminal part of titin and also peptides from other parts of titin, including the C-terminal part (after amino acid 34253), were identified in these analyses. No titin peptide was identified in the urine from healthy subjects. These results show that other parts of titin can be used as biomarkers. The analysis of the blood (serum) from 4 DMD patients using the "LC-MS/MS" approach demonstrated the presence of peptide 82-98 in the serum of just one patient. No titin peptide was identified in the sera of 6 healthy subjects tested using this same approach (data not shown).

The proteins were analyzed by western blot as described in Materials and Methods. The N-terminal titin fragment (marked as "Titin" on the Western blot) was detected in 2 out of 2 GRMD dogs, and was undetectable in the 2 healthy dogs analyzed (FIG. 5). C− negative control: urine sample from the healthy subject analyzed by two-dimensional electrophoresis; C+ positive control: urine sample from the DMD patient analyzed by two-dimensional electrophoresis.

Supplementary Studies

The peptides obtained from the digestion of proteins from urine of DMD patients and healthy patients were analyzed using the "LC-MS/MS" approach as described in Materials and Methods. Urine from 5 healthy individuals and 5 DMD patients was analyzed individually using the "LC-MS/MS" approach. The individual analysis enabled the detection of more titin peptides than in the pooled analysis as described previously and also demonstrated that a majority of the peptides identified corresponded to the N-terminal and C-terminal parts of titin. The peptides sequenced by MS/MS are shown in FIG. 6 with the identification score for each DMD patient.

The proteins were analyzed by Western blot as described in Materials and Methods. The N-terminal titin fragment (marked as "Titin" on the Western blot) was detected in 2 out of 2 mdx mice, and was undetectable in the 2 healthy mice analyzed (FIG. 7A). Several non-specific bands can be seen and are linked to the secondary antibody (FIG. 7B). C+ positive control: urine sample from the DMD patient analyzed by two-dimensional electrophoresis.

The proteins were analyzed by Western blot as described in Materials and Methods. The C-terminal titin fragment (marked as "Titin" on the Western blot) was detected in 5 out of 5 DMD patients, and was undetectable in the 4 healthy subjects analyzed (FIG. 8A). The C-terminal titin fragment (marked as "Titin" on the Western blot) was detected in 2 out of 2 dogs, and was undetectable in the 2 healthy dogs analyzed (FIG. 8B). The C-terminal titin fragment (marked as "Titin" on the Western blot) was detected in 2 out of 2 mdx mice, and was undetectable in the 2 healthy mice analyzed (FIG. 8C). C+ positive control: urine sample from the DMD patient analyzed by two-dimensional electrophoresis.

The proteins were analyzed by Western blot as described in Materials and Methods. The N-terminal titin fragment (marked as "N-ter titin" on the Western blot) was detected in all the mdx mice which had undergone physical exercise, with an increase 3 h after exercise (FIG. 9A). Moreover, the C-terminal titin fragment was only detected in the serum of mdx mice 3 h after exercise. This fragment was undetectable in the human control and in the sera of mice which did not undergo physical exercise (FIG. 9B). (NB: detecting the N-terminal titin fragment in the serum of mdx mice is not possible owing to the presence of only one primary antibody on the market (mouse anti-N-terminal titin) and hence the obligation to use an anti-mouse secondary antibody on mouse serum.) Moreover, the N-terminal titin fragment is still undetectable in the urine of healthy mice having undergone physical exercise for 30 minutes, or even for 1 h 30 min (FIG. 9C-D). C− human: human negative control: urine sample from a healthy subject; C+ human: human positive control: urine or serum sample from a DMD patient; C+ mouse: mouse positive control: urine sample from mdx mouse.

The serum proteins of mdx mice having undergone physical for exercise 30 min were separated on a 1D SDS-PAGE gel as described in Materials and Methods. The bands of interest (bands framed in FIG. 10A) were extracted manually and identified by MALDI-TOF/TOF mass spectrometry as an intermediate titin fragment (from amino acids 12994 to 16442; corresponding to amino acids 12132 to 15580 in the human sequence). This fragment was only detected in the sera of mdx mice having undergone physical exercise for 30 min and was undetected in healthy mice having undergone physical exercise for 30 min or even for 1 h 30 min (data not shown). The peptides sequenced by MALDI-TOF/TOF are shown in FIG. 10B with the identification score for each mdx mouse. Moreover, the size of this intermediate fragment (~3000 amino acids, i.e., ~300 kDa) identified by MALDI-TOF/TOF mass spectrometry corresponds to the size observed on the SDS-PAGE gels (~300 kDa).

In summary, all these experiments demonstrate that several fragments of titin (for example: N-terminal, C-terminal or "intermediate") are detected in both the serum and the urine of DMD patients, GRMD dogs, and mdx mice, and are undetected in the serum or the urine of healthy subjects, healthy dogs and healthy mice.

REFERENCES

Batchelor, C. L. and S. J. Winder (2006). "Sparks, signals and shock absorbers: how dystrophin loss causes muscular dystrophy." Trends Cell Biol 16(4): 198-205.

Bushby, K., R. Finkel, et al. "Diagnosis and management of Duchenne muscular dystrophy, part 1: diagnosis, and pharmacological and psychosocial management." Lancet Neurol 9(1): 77-93.

Charton, K., Danièle N., et al. (2010). "Removal of the calpain 3 protease reverses the myopathology in a mouse model for titinopathies." Hum Mol Genet 19(23): 4608-24

Cirak, S., V. Arechavala-Gomeza, et al. (2011). "Exon skipping and dystrophin restoration in patients with Duchenne muscular dystrophy after systemic phosphorodiamidate morpholino oligomer treatment: an open-label, phase 2, dose-escalation study." Lancet 378(9791): 595-605.

Le Rumeur, E., S. J. Winder, et al. "Dystrophin: more than just the sum of its parts." Biochim Biophys Acta 1804(9): 1713-22.

Lu, Q. L., T. Yokota, et al. "The status of exon skipping as a therapeutic approach to duchenne muscular dystrophy." Mol Ther 19(1): 9-15.

Muntoni, F., S. Torelli, et al. (2003). "Dystrophin and mutations: one gene, several proteins, multiple phenotypes." Lancet Neurol 2(12): 731-40.

Nicholson, G. A., G. J. Morgan, et al. (1986). "The effect of aerobic exercise on serum creatine kinase activities." Muscle Nerve 9(9): 820-4.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09933438B2). An electronic copy of the "Sequence Listing" will also be available from the USPTO upon request and payment of the fee set forth in 37 CFR 1.19(b)(3).

The invention claimed is:

1. A method for the detection of titin or a fragment thereof in a subject, comprising detecting the presence of titin or of one or more fragments of titin in a urine sample from said subject, said detecting comprising:
   a) contacting said urine sample with antibodies that bind to an epitope of titin and detecting the binding of said antibodies to said epitope; or
   b) specifically quantifying titin or one or more fragments thereof in said urine sample by mass spectroscopy.

2. The method according to claim 1, said method comprising measuring the level of expression of titin or of one or more fragments thereof in a second urine sample from a subject and comparing the level of titin or of said one or more fragments in said sample to the level of titin or of said one or more fragments of titin in a sample previously taken from the same subject.

3. The method according to claim 1, said method comprising:
   a) measuring the level of expression of titin or of one or more of its fragments in a urine sample, by means of which a reference level is determined (control level); and
   b) measuring the level of expression of said titin or of said fragment(s) in a second urine sample taken from the same subject at a time after the administration of a therapeutic treatment (test level); and
   c) comparing the control level and the test level.

4. The method according to claim 1, wherein the antibody binds to an epitope of the N-terminal titin fragment of approximately 300 amino acids or an epitope of the C-terminal titin fragment of approximately 150 amino acids.

5. A diagnostic kit comprising an antibody for detecting titin and one or more fragments of titin selected from SEQ ID NOs: 12-30 or a fragment between amino acids 12132 and 15880 of SEQ ID NO: 1 or SEQ ID NOs: 31-45 and instructions for implementing the method according to claim 1.

6. The method according to claim 1, wherein said method comprises quantifying titin or one or more fragments thereof in said urine sample by mass spectroscopy.

7. The method according to claim 6, wherein said mass spectroscopy is multiple reaction monitoring mass spectroscopy or MALDI-TOF/TOF mass spectroscopy.

8. The method according to claim 7, wherein said mass spectroscopy is multiple reaction monitoring mass spectroscopy.

9. The method according to claim 7, wherein said mass spectroscopy is MALDI-TOF/TOF mass spectroscopy.

* * * * *

UNITED STATES PATENT AND TRADEMARK OFFICE
CERTIFICATE OF CORRECTION

PATENT NO. : 9,933,438 B2  
APPLICATION NO. : 14/431030  
DATED : April 3, 2018  
INVENTOR(S) : Rouillon et al.

Page 1 of 1

It is certified that error appears in the above-identified patent and that said Letters Patent is hereby corrected as shown below:

In the Specification

Column 4,
Line 15, "(TITIN HUMAN" should read --(TITIN_HUMAN--.

Column 5,
Line 13, "(TITIN Mouse" should read --(TITIN_Mouse--.

Signed and Sealed this
Twenty-third Day of April, 2019

Andrei Iancu
*Director of the United States Patent and Trademark Office*